(12) United States Patent

Hoodless et al.

(10) Patent No.: US 12,636,061 B2

(45) Date of Patent: May 26, 2026

(54) ELECTROSURGICAL GENERATOR AND SYSTEM

(71) Applicant: GYRUS MEDICAL LIMITED, Cardiff (GB)

(72) Inventors: Richard John Hoodless, St Mellons (GB); Ben Clarke, St Mellons (GB)

(73) Assignee: GYRUS MEDICAL LIMITED, St Mellons (GB)

( * ) Notice: Subject to any disclaimer, the term of this patent is extended or adjusted under 35 U.S.C. 154(b) by 565 days.

(21) Appl. No.: 17/370,649

(22) Filed: Jul. 8, 2021

(65) Prior Publication Data

US 2022/0039857 A1 Feb. 10, 2022

(30) Foreign Application Priority Data

Aug. 10, 2020 (GB) .................................... 2012400

(51) Int. Cl.
*A61B 18/12* (2006.01)
*A61B 18/00* (2006.01)

(52) U.S. Cl.
CPC .............................. *A61B 18/1206* (2013.01); *A61B 2018/00744* (2013.01); *A61B 2018/00791* (2013.01);
(Continued)

(58) Field of Classification Search
CPC ........ A61B 2218/002; A61B 2218/007; A61B 18/1206; A61B 2018/00791
See application file for complete search history.

(56) References Cited

U.S. PATENT DOCUMENTS

2011/0137308 A1* 6/2011 Woloszko .......... A61B 18/1485
606/41
2015/0313666 A1* 11/2015 Aljuri ................ A61B 18/1485
606/41
(Continued)

FOREIGN PATENT DOCUMENTS

GB 2406793 A 4/2005
JP H04-22354 A 1/1992
JP 2007-252909 A 10/2007

OTHER PUBLICATIONS

Jan. 25, 2021 Search Report issued in British Patent Application No. GB2012400.4.

(Continued)

*Primary Examiner* — Michael F Peffley
*Assistant Examiner* — Samantha M Good
(74) *Attorney, Agent, or Firm* — Oliff PLC

(57) ABSTRACT

An electrosurgical system includes an RF electrosurgical generator, an electrosurgical instrument, and a pump. The radio frequency (RF) electrosurgical generator includes: an output socket for providing a RF output signal to an electrosurgical instrument according to an operating mode of the generator; and an output port arranged to output and return a loop signal for controlling a pump, wherein the generator is configured to generate the loop signal based at least in part on the operating mode of the generator. A method of controlling a pump in an electrosurgical system includes generating a loop signal at an electrosurgical generator based at least in part on an operating mode of the generator; outputting the loop signal to a loop cable; sensing, using a sensing device, the loop signal from the loop cable; and controlling the pump based on an output of the sensing device.

12 Claims, 3 Drawing Sheets

(52) U.S. Cl.
    CPC .............. *A61B 2018/00863* (2013.01); *A61B*
        *2218/002* (2013.01); *A61B 2218/007* (2013.01)

(56)                    References Cited

U.S. PATENT DOCUMENTS

2017/0010619 A1      1/2017  Foster et al.
2017/0020594 A1*     1/2017  Ishikawa ............ A61B 18/1206
2018/0071012 A1*     3/2018  Kucklick ............. A61B 18/148
2019/0159825 A1      5/2019  Frampton et al.

OTHER PUBLICATIONS

Dec. 6, 2022 Office Action issued in Japanese Patent Application
No. 2021-112864.
Feb. 28, 2023 Office Action issued in Japanese Patent Application
No. 2021-112864.
May 13, 2024 Office Action issued in Great British Patent Appli-
cation 2012400.4.
May 20, 2025 Office Action issued in German Patent Application
No. 10 2021 118 891.1.

* cited by examiner

ELECTROSURGICAL GENERATOR AND SYSTEM

TECHNICAL FIELD

Embodiments of the present invention described herein relate to an RF electrosurgical generator, and an RF electrosurgical system comprising an RF electrosurgical generator.

BACKGROUND TO THE INVENTION AND PRIOR ART

Electrosurgical instruments provide advantages over traditional surgical instruments in that they can be used for coagulation and tissue sealing purposes. Electrosurgical instruments are often used with fluid management devices or systems, such as a pump or a suction source.

One prior art arrangement is known from US 2017/ 106199 A1, which describes a system including a pump, and surgical devices such as a shaver and a RF device. The system includes an inflow tube for transporting surgery washing fluid from the pump to a body cavity, and an outflow tube for suctioning fluid out of the body cavity to the pump. Various information from elements of the system may be used to change the flow rate and/or pressure of the surgical fluid being provided to or suctioned from the body cavity. If the surgical devices are manufactured by the same manufacturer of the pump system, there may be two-way communication between the surgical devices and the pump. Therefore, the performance parameters of the surgical device can be communicated to a pump control processor to control the flow rate or pressure of the surgical fluid. If the pump is utilized with "third party" surgical devices (e.g. surgical devices from a manufacturer different to the manufacturer of the pump), the surgical devices may be connected to power outlets located on the pump housing. The pump housing may have current and/or voltage sensing devices to sense a waveform of power drawn by the unrecognized surgical devices when operated. Changes in the waveform can be used to differentiate between when the surgical device is on or off, and this information may be used to control the flow rate or pressure of the surgical fluid.

SUMMARY OF THE INVENTION

The present disclosure provides an improved way of activating and controlling a third-party pump in an electrosurgical system. The system includes an electrosurgical generator, a pump and an electrosurgical instrument. The instrument is able to perform various operations, such as electrosurgical coagulation, electrosurgical ablation, and/or mechanical cutting. The generator provides the appropriate RF signal and/or other signals to the instrument via a signal cord. The pump is connected to the instrument via tubes in order to provide irrigation and suction at the instrument. The generator determines whether the pump should be activated or triggered, for example, by internally detecting whether the generator is providing signals to the instrument over the signal cord. If it is determined that the pump should be activated, the generator generates a loop signal. The generator outputs the loop signal to a cable loop that is coupled to the generator, the cable loop being separate to the signal cord. A sensing device of the pump senses the loop signal passing through the cable loop. The pump detects the loop signal and triggers the pump to activate the irrigation and suction functionalities of the pump. The generator can control the pump flow rate of the pump by generating a loop signal of an appropriate level of current. The required flow rate from the pump may depend on the operations (e.g. coagulation, ablation, and/or mechanical cutting) being performed by the system. The generator generates the loop signal to have a current level that is proportional to the required pump flow rate. The sensing device senses the current level of the loop signal passing through the cable loop. The pump detects the current of the loop signal from the sensing device, and controls the pump flow rate in proportion to the sensed current.

Advantageously, the system has improved control over the operation of the third-party pump. For example, in other arrangements, the sensing device may attempt to sense the current through the signal cord that delivers the RF signal to the electrosurgical instrument. However, it is difficult to detect the current through the signal cord due to the signal cord being heavily screened or shielded from emissions interference. Moreover, the signal cord may be too large in diameter to accommodate most third party sensing devices. However, if a separate loop signal is outputted over a dedicated loop cable, it is easier for the sensing device to detect the current through the loop cable. In particular, the loop cable does not require as much shielding or screening as the signal cord, therefore it is easier for the sensing device to detect the current through the loop cable to control the pump. Furthermore, the loop cable may have a smaller diameter than the signal cord and therefore accommodate a wider range of third party sensing devices.

In view of the above, a first aspect of the present invention provides a radio frequency (RF) electrosurgical generator comprising an output socket for providing a RF output signal to an electrosurgical instrument according to an operating mode of the generator, and an output port arranged to output and return a loop signal for controlling a pump. Furthermore, the generator is configured to generate the loop signal based at least in part on the operating mode of the generator. Advantageously, such an arrangement generates a separate loop signal for controlling the pump, and outputs the loop signal from a separate output port. This provides improved control over third party pumps, since the current of the loop signal can be more easily detected.

In one embodiment, the RF electrosurgical generator comprises a loop cable coupled to the output port. In a further example, the loop cable comprises a first end coupled to an output side of the output port, and a second end coupled to a return side of the output port. This allows for the loop signal to be conducted through the loop cable in a closed loop. Advantageously, the loop signal can be sensed by a sensing device of a pump, without requiring a direct electrical connection between the pump and the generator. As such, it is easier and safer to use the generator with a variety of third-party pumps.

In one embodiment, the RF electrosurgical generator is configured to generate the loop signal based at least in part on a power level of the RF output signal and/or the mechanical shaving signal. Advantageously, the loop signal can be used to dynamically control the pump so that the pump provides an appropriate amount of irrigation and suction based on how the electrosurgical instrument is being used.

In one embodiment, the RF electrosurgical generator is configured to receive a command signal indicative of a user-requested change in the operation of the pump, and to generate the loop signal based at least in part on the command signal. Advantageously, this allows a user of the electrosurgical instrument can request specific changes or adjustments to the operation of the pump.

In one embodiment, the RF electrosurgical generator is configured to receive a sensor output signal from a temperature sensor at the electrosurgical instrument, and to generate the loop signal based at least in part on the sensor output signal. Advantageously, the generator can control the pump to appropriately adjust the operation of the pump based on the temperature at the instrument, for example, to provide cooling at the instrument if the temperature is too high.

In one embodiment, the RF electrosurgical generator determines whether the pump requires activating based at least in part on the operating mode, and then generates the loop signal if the pump requires activating. Advantageously, the pump can be dynamically activated and deactivated based on whether the generator is active in an operating mode. As such, the pump may be controlled so that it not unnecessarily kept active, thereby reducing energy wastage.

In one embodiment, the RF electrosurgical generator is configured to generate the loop signal, such that a current level of the loop signal exceeds a threshold current level if it is determined that the pump requires activating. Advantageously, this ensures that the loop signal is of large enough magnitude to be detected by a current sensing device.

In one embodiment, the RF electrosurgical generate further comprises user input means for inputting the threshold current level. Different current sensing devices may have different threshold settings for sensing currents. Therefore, the user input means enables a user to choose an appropriate threshold setting, so that the generator can be used with a wide variety of third-party current sensing devices.

In one embodiment, the RF electrosurgical generator generates the loop signal by first determining a pump flow rate based on one or more of the operating mode, the power levels, the command signal or the sensor readout signal. The RF electrosurgical generator then generates the loop signal to have a current level corresponding to the pump flow rate. Advantageously, the pump flow rate of the pump can be dynamically adjusted by generator via the loop signal, depending on the amount of suction and irrigation that is expected to be required at the instrument.

In one embodiment, the RF electrosurgical generator is configured to generate the loop signal based on information indicative of a current-response characteristic of the pump. Advantageously, this ensures that the loop signal is of an appropriate magnitude of current to instruct the pump to activate and provide the required pump flow rate.

In one embodiment, the RF electrosurgical generator further comprises user input means for inputting or selecting the information indicative of the current-response characteristic. Different pumps may have current-response characteristics. In particular, different pumps may provide a different pump flow rate for a given current level of the loop signal, or increase the pump flow rate by different amounts per a unit increase in the current level, or activate suction and irrigation at different threshold current levels. Therefore, the user input means enables a user to choose an appropriate current-response characteristic corresponding to the type of pump that is being used. This ensures that the loop signal is of an appropriate magnitude to instruct the pump to activate and provide the required pump flow rate. Moreover, the user input means allows the generator to be used with a wide variety of third-party current sensing devices.

In second aspect of the present invention, there is provided an electrosurgical system comprising an RF electrosurgical generator according the first aspect above, an electrosurgical instrument, and a pump.

In one embodiment, the electrosurgical system comprises a sensing device arranged to sense the loop signal and provide a signal indicative of the loop signal to the pump.

In a third aspect of the present invention, there is also provided a method of controlling a pump in an electrosurgical system, the method comprising: generating a loop signal at an electrosurgical generator based at least in part on an operating mode of the generator; outputting the loop signal to a loop cable; sensing the loop signal from the loop cable using a sensing device; and controlling the pump based on the sensor output. Advantageously, the loop signal can be more easily detected from the loop cable, which provides for improved control over the pump.

BRIEF DESCRIPTION OF THE DRAWINGS

Embodiments of the invention will now be further described by way of example only and with reference to the accompanying drawings, wherein like reference numerals refer to like parts, and wherein.

DESCRIPTION OF THE EMBODIMENTS

Figure 1A:
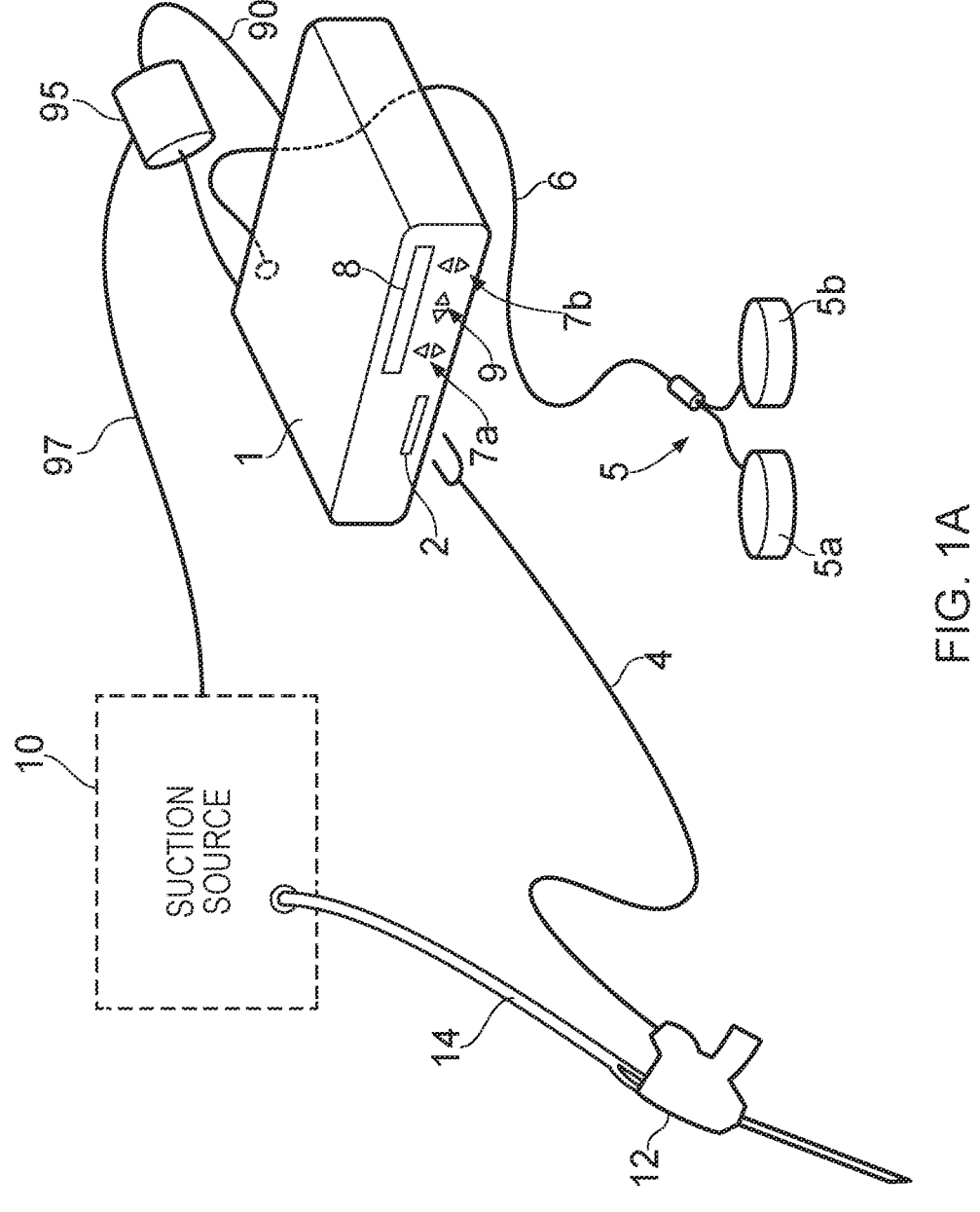
FIG. 1A illustrates an electrosurgical system including an electrosurgical instrument according to an embodiment of the present invention.
Figure 1B:
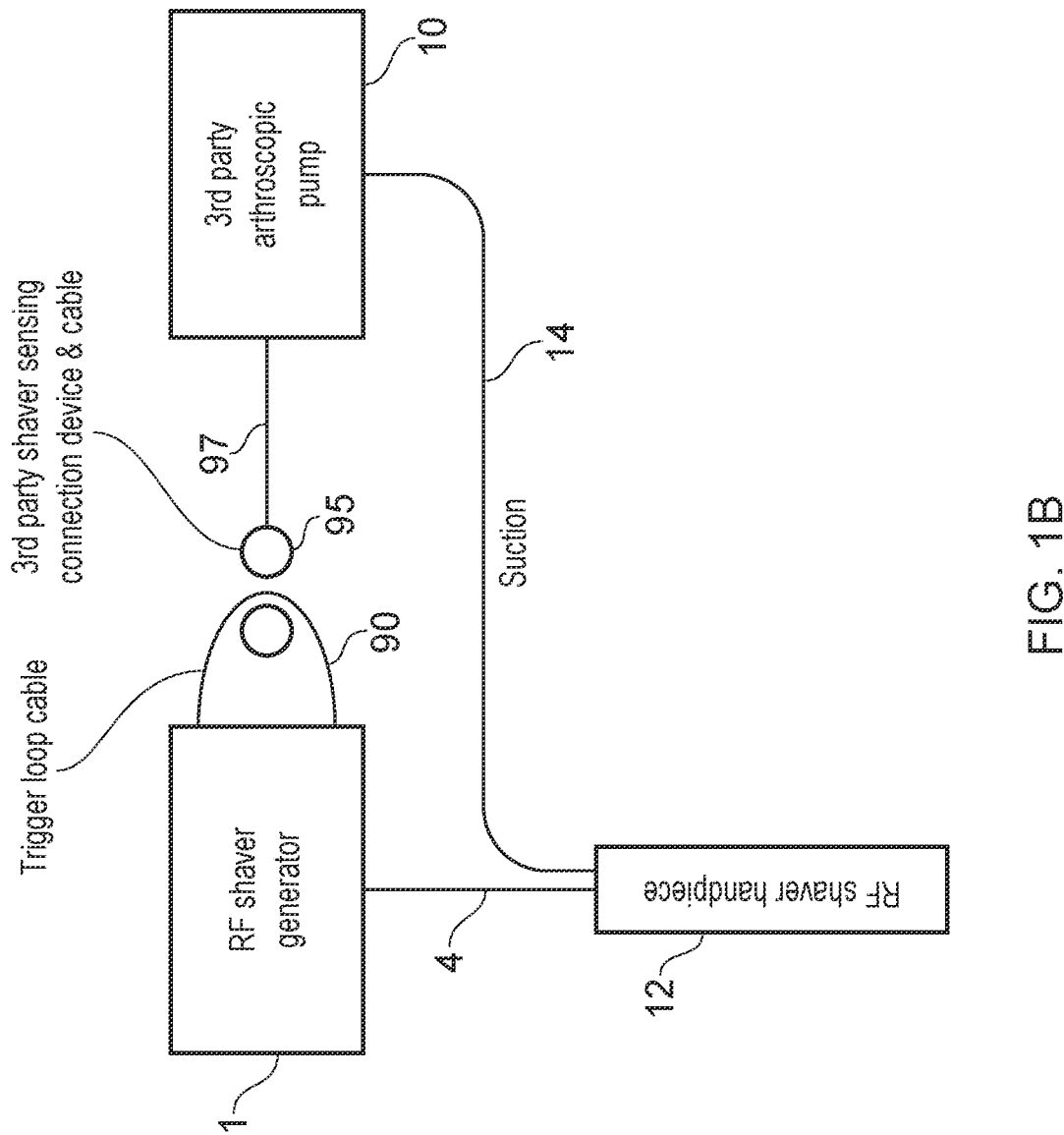
FIG. 1B is a schematic diagram showing the electrosurgical system of FIG. 1A.

Referring to the drawings, FIG. 1A shows an electrosurgical system including an electrosurgical generator 1, an electrosurgical instrument 12 and an irrigation fluid and suction source 10. The irrigation fluid and suction source 10 is also referred to herein as a "pump" 10. Furthermore, FIG. 1B shows a schematic diagram of the electrosurgical system of FIG. 1A.

The generator 1 comprises an output socket 2 for providing output signals, via a connection cord 4, to the electrosurgical instrument 12. The generator 1 is configured to generate the output signals. In particular, the generator 1 is configured to generate and supply a RF signal to the instrument 12 in order to enable electrosurgical functionalities at the instrument 12. More particularly, the generator 1 is configured to generate and supply a RF signal of appropriate power to the instrument 12 in order to provide coagulation electrosurgical functionality or ablation electrosurgical functionality at the instrument 12.

In a coagulation mode, the generator 1 generates a RF signal having a first power level in order to provide coagulation electrosurgical functionalities at the instrument 12. In an ablation mode, the generator 1 generates a RF signal having a second power level in order to provide ablation electrosurgical functionalities at the instrument 12. The first power level is within a coagulation range of power levels that enables electrodes at a distal end effector of the instrument 12 to perform coagulation functionalities. The second power level is within an ablation range of power levels that enables said electrodes to perform ablation functionalities. The ablation range of power levels may typically comprise power levels higher than the power levels in the coagulation range of power levels.

The generator 1 is also configured to generate and supply a mechanical cutting signal to the instrument 12 via the connection cord 4, in order to provide mechanical cutting functionalities at the instrument 12. In the coagulation and ablation operating modes, the RF signal and the mechanical cutting signal may be generated and supplied to the instrument 12 simultaneously in order to provide simultaneous electrosurgical and mechanical cutting functionalities at the instrument 12. Optionally, in other operating modes, the generator 1 may generate only one of the RF or mechanical cutting signals at a time, to provide one of the electrosurgical functionalities or the mechanical cutting functionality at the instrument 12.

Figure 2:
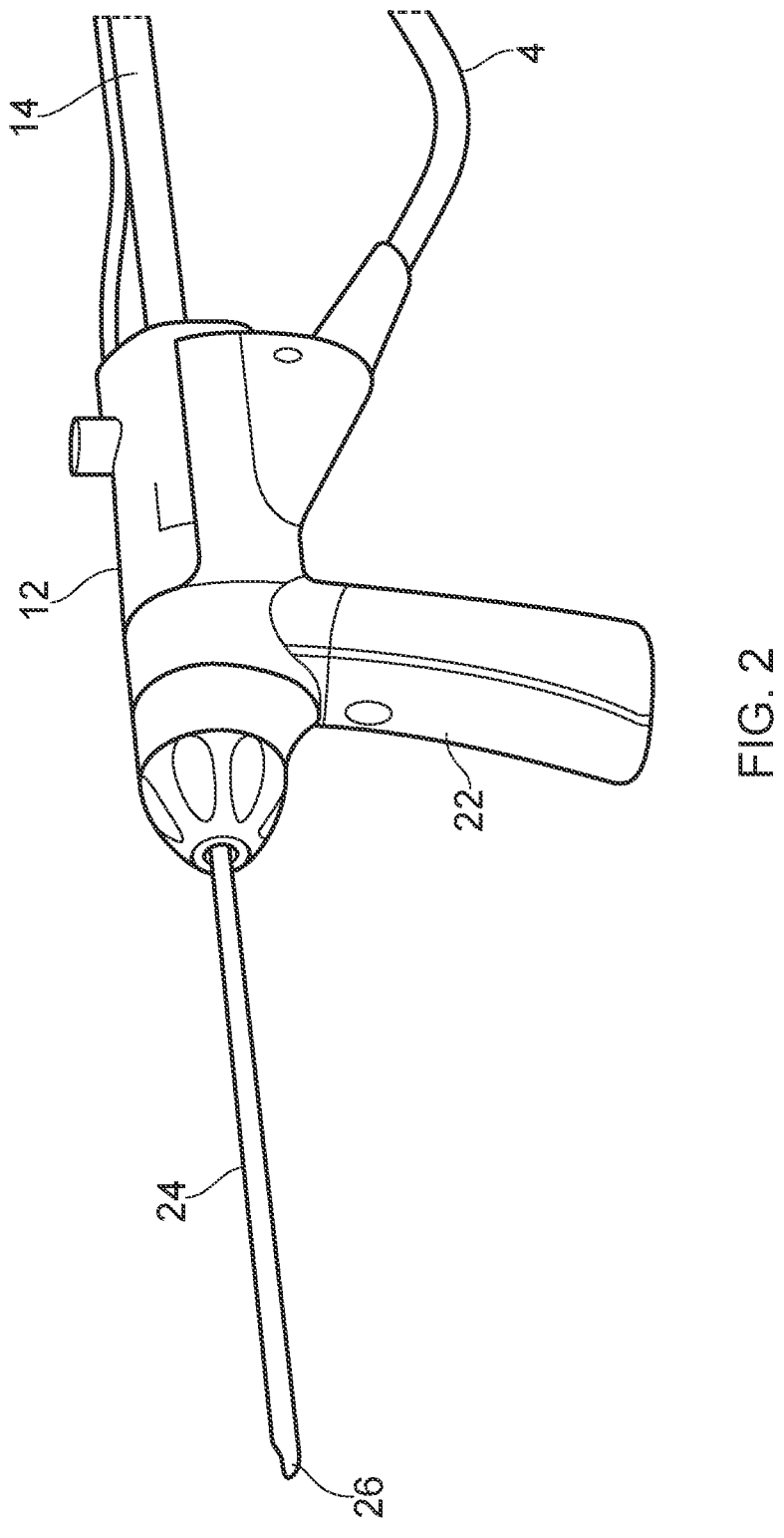
FIG. 2 is a side view of an electrosurgical instrument according to an embodiment of the present invention.

FIG. 2 shows the electrosurgical instrument 12 in more detail. The instrument 12 includes a proximal handle portion 22, a hollow shaft 24 extending in a distal direction away from the proximal handle portion, and a distal end effector assembly 26 at the distal end of the outer shaft. The power connection cord 4 connects the instrument to the RF generator 1, whereas the tubes 14 connect the instrument to the irrigation and suction source 10. The instrument 12 may further be provided with activation buttons (not shown), to allow the surgeon operator to activate either the mechanical cutting function of the end effector, and/or the electrosurgical functions of the end effector. Reference is made to UK patent application no. GB1903712.6 which describes the end effector assembly 26 in more detail, and how said mechanical cutting and electrosurgical functionalities may be simultaneously achieved by the end effector assembly 26.

In some embodiments, the electrosurgical instrument 12 may also comprise one or more instrument sensors (not shown). In one example, the instrument sensors include a first temperature sensor arranged to sense the temperature in the locality or environment of the instrument 12. As such, when the instrument 12 is being used at a surgical site, the first temperature sensor senses the temperature of the surgical site. Additionally or alternatively, the instrument sensors may include a second temperature sensor arranged to sense the temperature of the instrument 12 itself, e.g. the temperature of the distal end effector assembly 26. In such embodiments, the generator 1 is configured to receive output signals from the one or more instrument sensors, over the connection cord 4.

Referring back to FIG. 1, activation of the generator 1 may be performed from the instrument 12 via a handswitch (not shown) on the instrument 12, or by means of a footswitch unit 5 connected separately to the rear of the generator 1 by a footswitch connection cord 6. In the illustrated embodiment of FIG. 1, the footswitch unit 5 has two footswitches 5a and 5b for selecting or activating the coagulation mode or the cutting/vaporisation (ablation) mode of the generator 1, respectively. For example, a first footswitch 5a may be actuated to select the coagulation mode, and a second footswitch 5b may be actuated to select the ablation mode. In some examples, the footswitch unit 5 and the generator 1 is arranged such that only one of the coagulation and ablation modes is selectable at any one time.

Mechanical cutting may be automatically provided at the instrument 12 upon activation of the coagulation or the ablation mode. Alternatively or additionally, mechanical cutting may be separately provided by actuation of a separate button or switch, either on the footswitch unit 5 or the handswitch (not shown). It will be appreciated that embodiments in which activation of the generator 1 is performed via a handswitch may achieve the same functionality as embodiments in which the generator 1 is activated via the footswitch unit 5.

The generator front panel comprises pairs of push buttons 7a and 7b. The pair of push buttons 7a may be used for setting the ablation power level within the ablation power range. The pair of push buttons 7b may be used for setting the coagulation power level within the coagulation power range. The front panel of the generator 1 also comprises a display 8 that indicates the ablation and coagulation power levels set. In some embodiments, an additional pair of mode-selecting push buttons 9 may also be provided as an alternative means for selecting between the ablation and coagulation modes.

The electrosurgical system of FIG. 1 further comprises a loop cable 90 coupled to the generator 1. In particular, the generator 1 comprises a loop signal output port (not shown), and the loop cable 90 is coupled to the generator 1 via the loop signal output port. The loop signal output port comprises an output or send side for outputting or sending a loop signal to the loop cable 90. The loop signal output also comprises a return side for returning the loop signal from the loop cable 90. The loop cable 90 has a first end and a second end. The first end is coupled to the output side of the loop signal output port to receive a loop signal, and the second end is coupled to the return side to return a loop signal. As such, the loop cable 90 is arranged to conduct a loop signal outputted from the generator 1 in a closed loop.

In some embodiments, the loop cable 90 is detachably coupled with the generator 1 via the loop output port, thereby forming a separate component of the electrosurgical system. In other embodiments, the loop cable 90 is integrally attached to the generator 1, e.g. soldered or welded to the generator 1, thereby forming part of the generator 1.

The generator 1 is configured to generate the loop signal when irrigation and suction functionalities of the pump 10 are required at the instrument 12. Moreover, the generator 1 is configured to generate the loop signal to have a current level that is proportional to a required amount of irrigation and suction at the instrument 12. The amount of irrigation refers to the rate of flow of the irrigation fluid through the irrigation tube, and the amount of suction refers to the rate of fluid flow through the suction tube. The rate of flow of the irrigation fluid and the rate of fluid flow through the suction tube are more generally referred to as the pump flow rate.

The generator 1 is configured to pass the loop signal through the loop cable 90. The loop signal may also be referred to as a control signal, or a pump control signal. The generator 1 outputs the loop signal to the output side of the loop signal output, such that the loop signal conducts through the loop cable 90 and returns to the generator 1 at the return side of the loop signal output. Therefore, the generator 1 and the loop cable 90 is arranged such that the loop signal conducts through the loop cable 90, e.g. in a closed loop.

Although not shown in FIG. 1, the generator 1 may also comprise a power inlet port to receive electrical power from a power supply. The power inlet port is arranged to couple to a power supply via a power cable. Furthermore, the power inlet port and the power cable is separate to the loop signal output port and the loop cable.

The pump 10 is connected to the instrument 12 via irrigation and suction tubes 14. The pump 10 is configured to introduce or pump surgical fluid to the instrument 12 via the irrigation and suction tubes 14. The pump 10 is also configured to provide suction at the instrument 12 via the irrigation and suction tubes 14. As such, when the instrument 12 is being used at a surgical site, the pump allows surgical fluid to be introduced to the surgical site via the tubes 14 and the instrument 12, and the pump 10 provides a source of suction at the surgical site via the tubes 14 and the instrument 12. Introducing the surgical fluid to the surgical site may improve the surgeon's view of the surgical site and create more space at the surgical site. Furthermore, the suction may allow for the removal of the surgical fluid, as well as other fluids, tissue fragments, bubbles or other debris in the vicinity of the surgical site.

The electrosurgical system of FIG. 1 further comprises a current sensing device 95. In the illustrated embodiment of FIG. 1, the current sensing device 95 is inductively coupled to the loop cable 90, between the first and second ends of the loop cable 90. In other words, there is no direct electrical contact between the current sensing device 95 and the loop cable 90. The current sensing device 95 is also coupled to the pump 10 via a sensor cable 97. In some embodiments, the current sensing device 95 is detachably coupled with the pump 10 and therefore forms a separate component of the electrosurgical system. In other embodiments, the current sensing device 95 is integrally attached to the pump 10, thereby forming part of the pump 10.

The current sensing device 95 is configured to sense or detect the loop signal passing through the loop cable 90. In particular the current sensing device 95 detects the current level of the loop signal from the loop cable 90. The current sensing device 95 outputs the detected current level of the loop signal to the pump 10. The pump 10 is configured to activate its irrigation and suction functionalities in response detecting the presence of the loop signal via the current sensing device 95. Additionally, the pump 10 is configured to control its pump flow rate based on the detected current level of the loop signal. In particular, the pump 10 may control its flow rate to be proportional to the detected current level of the loop signal. For example, if a low current level is sensed, the pump 10 may provide a correspondingly low pump flow rate. If a higher current level is sensed, the pump 10 may provide a correspondingly higher pump flow rate.

Accordingly, the generator 1 is able to control the operation of the pump 10 in order to provide an appropriate amount of suction and irrigation at the surgical site via the instrument 12. In operation, the generator 1 generates a loop signal if irrigation and suction functionalities are required at the instrument 12. In particular, the generator 1 generates a loop signal to have a current level that reflects the required operation of the pump 10 (e.g. that reflects whether the pump should be activated/triggered, and what the pump flow rate should be). The generator 1 outputs the loop signal to the loop cable 90. The pump 10 detects the presence of the loop signal via the current sensor 95 and activates its irrigation and suction functionalities. The pump 10 also controls its pump flow rate according to the detected current level of the loop signal. In particular, the pump 10 may adjust the speed or rate of flow of the irrigation fluid and the fluid through the suction tube based on the detected current level.

As explained above, the generator 1 generates the loop signal when irrigation and suction functionalities are required at the instrument 12, i.e. when the pump 10 requires activation or triggering. The pump 10 may require activation/triggering when the generator becomes active by entering an operating mode, such as the coagulation electrosurgical mode, the ablation electrosurgical mode, the mechanical cutting mode, or any combination thereof. As such, the generator 1 is configured to generate the loop signal when the generator 1 is operating in one of the operating modes. In other words, the generator 1 generates the loop signal when the generator 1 is providing RF and/or mechanical cutting signals to the instrument 12 via the connection cord 4. However, if the generator 1 is not operating in any of the above operating modes (i.e. the generator is not providing any RF or mechanical shaving signals to the instrument 12), no suction or irrigation may be required, and therefore the generator 1 may not generate the loop signal.

The required pump flow rate may be dependent on the operating mode of the generator 1. In particular, the required pump flow rate may depend on whether the generator 1 is operating in the coagulation electrosurgical mode, the ablation electrosurgical mode, the mechanical cutting mode, or any combination thereof. This is because some operating modes or combinations of operating modes may require a greater pump flow rate than others. For example, using the ablation mode may result in more debris at the surgical site in comparison to using the coagulation mode, therefore requiring a higher pump flow rate. Moreover, the required or optimal pump flow rate may also depend on the power level of the RF signal provided by the generator 1 whilst operating in the present operating mode, e.g. as set using the pairs of push buttons 7a and 7b. For example, a higher power level may result in relatively more debris at the surgical site, therefore requiring a higher pump flow rate. Optionally, the optimal pump flow rate may also depend on the power level of the mechanical shaving signal being supplied to the instrument 12.

Since the generator 1 has access to information regarding its present operating mode and the power levels of the signals, the generator 1 can generate a loop signal of an appropriate current level that reflects the required pump flow rate. In some embodiments, the generator 1 may first determine or calculate the required pump flow rate (e.g. as a unit of $m^3/s$) based on the present operating mode and the power levels of the RF and/or mechanical cutting signals. The generator 1 may be programmed using any appropriate technique to determine a required or optimal pump flow rate based on the operating mode and the signal power levels. As one example, the generator 1 may comprise one or more look-up tables to determine an appropriate pump flow rate from the set of operating modes, and from the power levels of the RF and mechanical shaving signals within those operating modes. After determining the required pump flow rate, the generator 1 may generate the loop signal to have a current level according to the determined pump flow rate.

In some embodiments of the electrosurgical system, a user may perform separate commands in order to further control the operation of the pump 10. In such embodiments, the instrument 12 and/or the footswitch unit 5 comprises additional buttons (not shown). A user can actuate one of the additional buttons to request a temporary change in the operation of the pump 10. The generator 1 may then receive a corresponding command signal from the instrument 12 over the cord 4 or from the footswitch unit 5 over connection cord 6. The command signal is indicative of the user-requested change in the operation of the pump 10. The generator 1 may store a predetermined response to the command signal, such as increasing or decreasing the required pump flow rate and the loop signal current by a predetermined amount. In one example, the command signal may indicate a request for a temporary increase in the pump flow rate (e.g. a "Flow+" command), in order to clear fluid and debris from the surgical site. The generator 1 may appropriately increase the current level of the loop signal to reflect the new required pump flow rate. Alternatively, the generator 1 may start generating the loop signal in response to the command signal to activate the pump, if the loop signal is not already being generated. As such, the generator 1 is further configured to generate the loop signal based on the command signal, which is indicative of a user requested change in the operation of the pump 10. The instrument 12, generator 1 and/or the footswitch unit 5 may comprise any number of additional buttons for the user to request any other change in the operation of the pump 10.

In embodiments where the instrument 12 comprises one or more instrument sensors, the generator may also be configured to generate the loop signal based on the outputs of the instrument sensors. For example, if the output of one of the first or second temperature sensors at the instrument 12 is higher than a respective temperature threshold, this may indicate that a higher pump flow rate is required to provide cooling to the surgical site or the instrument 12. Therefore, if the generator 1 is not already generating the loop signal, the generator 1 may generate the loop signal after determining that the temperature sensor output is higher than the temperature threshold. If the generator 1 is already generating the loop signal (e.g. the generator 1 is operating in an operating mode), the generator 1 may increase the current level of the loop signal upon determining that the temperature sensor output is higher than the temperature threshold.

In view of the above, the generator 1 can be configured to generate the loop signal based on one or more of the operating mode, power level, command signals or sensor readout signals, so that the current level of the loop signal reflects the required operation of the pump 10.

Different types of current sensors 95 may have different current sensing thresholds. For example, a current sensor type x may only be able to sense a current above a threshold of 0.05 mA. A current sensor of type Y may only be able to sense a current above a threshold of 0.01 mA.

Therefore, in some embodiments, the generator 1 comprises a sensor threshold knob (not shown) on the generator housing. The sensor threshold knob can be used by a user to program the current sensing threshold of the current sensor 95 into the generator 1. For example, if the current sensor 95 is the sensor type X, a user can select the current sensing threshold of 0.05 mA using the sensor threshold knob. Under this setting, when the generator 1 determines that suction and irrigation is required, the generator 1 will generate a loop signal that has a current level of at least 0.05 mA. Accordingly, the current sensor 95 will be able to sense the loop signal and output the detected current level of the loop signal to the pump 10, and the pump 10 will activate/trigger. Although one example is provided above, it will be appreciated that any other appropriate current sensor threshold may be programmed into the generator 1 in order to enable the generator 1 to operate with any other suitable type of current sensor. It should also be appreciated that the sensor threshold knob may be replaced by any other suitable means for programming the current sensor threshold into the generator 1 (e.g. a pair of push buttons). Furthermore, the sensor threshold programmed into the generator may be displayed on the display 8.

Different types of pump 10 may have different pump activation thresholds. For example, a pump type A may only activate suction and irrigation functionalities if the detected current level from the sensor 95 exceeds a pump activation threshold of 0.1 mA, whereas a pump type B may only activate suction and irrigation if the detected current level from the current sensor 95 exceeds a pump activation threshold of 0.2 mA.

Therefore, in some embodiments, the generator 1 comprises a pump threshold knob (not shown) on the generator housing. The pump threshold knob can be used by a user to program the pump activation threshold of the pump 10 into the generator 1. For example, if the pump 10 is the pump type A, a user can select the pump activation threshold of 0.1 mA using the threshold knob. Under this setting, when the generator 1 determines that suction and irrigation is required, the generator 1 will generate the loop signal that has a current level of at least 0.1 mA. Accordingly, the current sensor 95 will output the detected current level of the loop signal to the pump 10, which will large enough magnitude to enable the pump 10 to activate. Although one example is provided above, it will be appreciated that any other appropriate activation threshold may be programmed into the generator 1 in order to enable the generator 1 to operate with any other suitable type of pump 10. It should also be appreciated that the pump threshold knob may be replaced by any other suitable means for programming the pump activation threshold into the generator 1 (e.g. a pair of push buttons). Furthermore, the present pump activation threshold programmed into the generator may be displayed on the display 8.

Different types of pump 10 may also have different pump flow rates for the same level of sensed current. For example, the pump type A may provide a pump flow rate of 0.2 m³/s at its pump activation threshold of 0.1 mA. The pump type A may then linearly increase the pump flow rate at a rate of 0.2 m³/s per 0.1 mA increase in the sensed current level. On the other hand, the pump type B may provide a pump flow rate of 0.3 m³/s at the pump activation threshold of 0.2 mA. The pump type B may then linearly increase the pump flow rate at a rate of 0.3 m³/s per 0.1 mA increase in the sensed current level.

Therefore, in some embodiments, the generator 1 further comprises a pump sensitivity knob (now shown) on the generator housing. The pump sensitivity knob may enable a user to select how much the pump 10 increases its flow rate per a unit amount of current (e.g. per 0.1 mA). For example, if the pump 10 is the pump type A, a user can select the flow rate "0.2 m³/s" using the pump sensitivity knob. A pump sensitivity setting of 0.2 m³/s indicates to the generator 1 that the pump 10 increases its flow rate by 0.2 m³/s per unit level of current (e.g. per 0.1 mA), starting at the pump activation threshold level of 0.1 mA. Under this setting, when the generator 1 determines that suction and irrigation is required, the generator 1 will generate a loop signal of an appropriate current so that the pump 10 provides the required pump flow rate. For example, the generator 1 may determine that a flow rate of 1.2 m³/s is required. Under the above pump sensitivity setting according to the pump type A (as well as the appropriate pump activation threshold setting), the generator 1 may generate the loop signal so that a current of 0.6 mA passes through the loop cable 90. Accordingly, the pump 10 may detect a current of 0.6 mA, and provide a pump flow rate of 1.2 m³/s. Although one example is provided above, it will be appreciated that any other appropriate pump sensitivity level may be programmed into the generator 1 in order to enable the generator 1 to operate with any other suitable type of pump 10. It should also be appreciated that the pump sensitivity knob may be replaced by any other suitable means for programming the pump activation threshold into the generator 1 (e.g. a pair of push buttons). Furthermore, the present pump sensitivity programmed into the generator may be displayed on the display 8.

In some embodiments, the current response characteristics of a discrete set of pump types may be pre-programmed into the generator 1. The current response characteristic is the characteristic between the sensed current and the amount of irrigation and suction provided by the pump, which encompasses the pump activation threshold and the pump sensitivity. In these embodiments, the generator 1 may comprise a knob or push buttons to enable a user to select the pump type. In such embodiments, the pump activation threshold knob and the pump sensitivity knob may be omitted.

Advantageously, the generator 1 can generate a loop signal of an appropriate magnitude to enable the current sensor 95 to detect the loop current, and to enable the pump 10 to provide the required pump flow rate. This allows the generator 1 and the instrument 12 to be used with a wide range of current sensor types and pump types from different manufacturers that may have different current response characteristics.

The above described arrangements of the electrosurgical system of FIG. 1 provide several advantages over other arrangements. For example, in a different arrangement, the current sensing device may be arranged to detect current passing through the connection cord 4. The current sensing device may infer a required amount of suction from the sensed current through the cord 4. This is because the current passing through the connection cord 4 may be dependent on the amount of power supplied to the instrument 12, in turn indicating an estimate of the required amount of irrigation or suction.

However, the cord 4 may be heavily screened or shielded in order to prevent emissions interference between the RF signal and mechanical cutting signals being simultaneously transmitted through the cord 4. An undesired effect of this screening may be that the accuracy of the current sensing device's current measurement is reduced. In particular, the current sensing device may be prevented from properly detecting when the mechanical shaving and/or electrosurgical RF functions are being used, and therefore it may be difficult to determine whether the pump requires activation and the required pump flow rate from the current sensor output.

Additionally, since the cord 4 is for propagating both RF and mechanical shaving signals, the diameter of the cord 4 may be relatively large. As such, the cord 4 may be too large in diameter to accommodate coupling to many current sensing devices.

Furthermore, if a user requests temporary changes to the pump flow rate, e.g. by selecting the "Flow+" function using the additional buttons at the instrument 12, the resulting current signals in the cord 4 may be too small in magnitude to be detected by the current sensing device.

Advantageously, with the arrangement of FIG. 1, the generator 1 uses a separate loop cable 90 to output a loop signal. The loop signal has a current level indicative of the required pump flow rate. The loop cable 90 is separate to cord 4 and does not carry the RF signal and the mechanical cutting signal. Therefore, the loop cable 90 does not require the same level of emissions screening as the cord 4, thereby allowing the loop signal and its current to be more easily detected by the current sensing device.

Furthermore, since the loop cable 90 does not carry the RF signal and the mechanical cutting signal, the diameter of the loop cable 90 may be made relatively smaller than the cord 4, thereby allowing for a wider variety of current sensing devices to be used. Moreover, since the RF generator 1 generates a separate loop signal, the user requested changes to the required pump flow rate can be more easily detected. Additionally, as the RF generator 1 generates a separate loop signal for controlling the pump, the RF generator 1 can be programmed to operate more optimally with a wider variety of pump types and current sensor types.

It should be appreciated that the above described embodiments may be implemented using any known hardware, software, and implementation techniques known by the skilled person. For example, the electrosurgical generator 1 may comprise any number of processors and signal generation circuits configured to operate as described above.

Various modifications whether by way of addition, deletion, or substitution of features may be made to above described embodiment to provide further embodiments, any and all of which are intended to be encompassed by the appended claims.

The invention claimed is:

1. An electrosurgical system comprising:
a radio frequency (RF) electrosurgical generator;
an electrosurgical instrument;
a pump; and
an inductive sensing device configured to sense a loop signal and provide a signal indicative of the loop signal to the pump;
wherein the RF electrosurgical generator comprises:
an output socket configured to provide a RF output signal to the electrosurgical instrument according to an operating mode of the generator; and
an output port configured to output and return the loop signal, distinct from the RF output signal, for controlling the pump through a loop cable coupled to the output port, the output port being arranged such that the loop signal is conducted in a closed loop without a direct electrical connection between the pump and the generator, wherein the loop signal does not deliver power to the pump and the electrosurgical instrument,
wherein the loop cable is arranged such that the loop signal for controlling the pump is inductively sensed by the inductive sensing device, and
wherein the generator is configured to generate the loop signal based at least in part on the operating mode of the generator.

2. The electrosurgical system of claim 1, wherein the loop cable comprises a first end coupled to an output side of the output port, and a second end coupled to a return side of the output port.

3. The electrosurgical system of claim 1, wherein the generator is further configured to generate the loop signal based at least in part on a power level of the RF output signal and/or a mechanical shaving signal.

4. The electrosurgical system of claim 1, wherein the generator is further configured to receive a command signal indicative of a user-requested change in the operation of the pump, and to generate the loop signal based at least in part on the command signal.

5. The electrosurgical system of claim 1, wherein the generator is further configured to receive a sensor output signal from a temperature sensor at the electrosurgical instrument, and to generate the loop signal based at least in part on the sensor output signal.

6. The electrosurgical system of claim 1, wherein the generator is configured to generate the loop signal by:
determining whether the pump requires activating based at least in part on the operating mode; and
generating the loop signal if the pump requires activating.

7. The electrosurgical system of claim 1, wherein the RF electrosurgical generator is configured to generate the loop signal, such that a current level of the loop signal exceeds a threshold current level if it is determined that the pump requires activating.

8. The electrosurgical system of claim 7, further comprising user input means for inputting the threshold current level.

9. The electrosurgical system of claim 1, wherein the generator is configured to generate the loop signal by:

determining a pump flow rate based on one or more of the operating mode, power levels, a command signal, or a sensor readout signal; and generating the loop signal to have a current level corresponding to the pump flow rate.

10. The electrosurgical system of claim 1, wherein the generator is further configured to generate the loop signal based on information indicative of a current-response characteristic of the pump.

11. The electrosurgical system of claim 10, further comprising user input means for inputting or selecting the information indicative of the current-response characteristic.

12. A method of controlling a pump in an electrosurgical system comprising an RF electrosurgical generator, an electrosurgical instrument, a pump, an inductive sensing device configured to sense a loop signal and provide a signal indicative of the loop signal to the pump and a radio frequency (RF) electrosurgical generator, the method comprising:

providing, via an output socket of the RF electrosurgical generator, a RF output signal to the electrosurgical instrument according to an operating mode of the generator;

generating a loop signal for controlling the pump at an the electrosurgical generator based at least in part on an operating mode of the generator, wherein the loop signal is distinct from the RF output signal;

outputting, from an output port configured to output and return the loop signal, the loop signal to a loop cable, the loop signal being conducted through the loop cable in a closed loop without a direct electrical connection between the pump and the generator, wherein the loop signal does not deliver power to the pump and an electrosurgical instrument;

inductively sensing, using a sensing device, the loop signal from the loop cable; and controlling the pump based on an output of the sensing device without a direct electrical connection between the pump and the generator.

* * * * *